(12) United States Patent
Ryan et al.

(10) Patent No.: US 9,309,916 B2
(45) Date of Patent: Apr. 12, 2016

(54) COIL DESIGN FOR IMPROVED ROTATIONAL PERFORMANCE

(71) Applicant: Boston Scientific Scimed, Inc., Maple Grove, MN (US)

(72) Inventors: Shawn Ryan, Upton, MA (US); Brian J. Intoccia, Nashua, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 14/278,138

(22) Filed: May 15, 2014

(65) Prior Publication Data
US 2014/0248964 A1 Sep. 4, 2014

Related U.S. Application Data

(63) Continuation of application No. 13/873,768, filed on Apr. 30, 2013, now Pat. No. 8,758,270, which is a continuation of application No. 12/884,401, filed on Sep. 17, 2010, now abandoned.

(60) Provisional application No. 61/247,330, filed on Sep. 30, 2009.

(51) Int. Cl.
| A61M 25/00 | (2006.01) |
| F16C 1/02 | (2006.01) |
| F16D 3/52 | (2006.01) |
| A61B 1/00 | (2006.01) |
| A61B 1/005 | (2006.01) |

(52) U.S. Cl.
CPC .............. *F16C 1/02* (2013.01); *A61B 1/0011* (2013.01); *A61B 1/0055* (2013.01); *F16D 3/52* (2013.01)

(58) Field of Classification Search
CPC ...... A61M 25/09; A61M 25/01; A61M 25/00
USPC .............. 600/433, 434, 585; 604/164.13, 523
See application file for complete search history.

(56) References Cited

U.S. PATENT DOCUMENTS

| 5,931,830 A * | 8/1999 | Jacobsen et al. .............. 604/523 |
| 7,413,563 B2 * | 8/2008 | Corcoran et al. ............. 604/523 |

* cited by examiner

*Primary Examiner* — Max Hindenburg
*Assistant Examiner* — Jonathan M Foreman
(74) *Attorney, Agent, or Firm* — Kacvinsky Daisak Bluni PLLC

(57) ABSTRACT

A coil for transmitting torque comprises a wire having a longitudinal axis and first and second longitudinal edges extending along the longitudinal axis, wherein the first longitudinal edge is formed with a first pattern and the second longitudinal edge is formed with a second pattern complementary to the first pattern, the first and second patterns being configured to interlock with one another when the wire is wound into a helical shape.

16 Claims, 5 Drawing Sheets

COIL DESIGN FOR IMPROVED ROTATIONAL PERFORMANCE

PRIORITY CLAIM

This application claims the priority to the U.S. Provisional Application Ser. No. 61/247,330, entitled "Coil Design for Improved Rotational Performance" filed Sep. 30, 2009. The specification of the above-identified application is incorporated herewith by reference.

BACKGROUND

Devices with flexible shafts are often required to guide endoscopes to target sites within a body lumen or cavity. Such a guide shaft provides a semi-rigid structure through which an endoscope may be passed without causing damage thereto. Criteria for guide shafts may vary according to the procedure being performed but may include, among others, a combination of varying levels of kink resistance, crush resistance, flexibility, etc. Although these flexible shafts are often formed as coils, the ability of many of these coils to transmit rotational forces along their lengths is insufficient for certain applications.

SUMMARY OF THE INVENTION

The present invention relates to a coil for transmitting torque comprising a wire having a longitudinal axis and first and second longitudinal edges extending along the longitudinal axis, wherein the first longitudinal edge is formed with a first pattern and the second longitudinal edge is formed with a second pattern complementary to the first pattern, the first and second patterns being configured to interlock with one another when the wire is wound into a helical shape.

DETAILED DESCRIPTION

The present invention, which may be further understood with reference to the following description and the appended drawings, relates to shaft devices through which endoscopes and other medical devices are positioned in body lumens and cavities. For example, the present devices and methods may be used to guide endoscopes into and through body lumens such as the duodenum, esophagus, large intestine, gastrointestinal tract, etc. It is noted that, although the exemplary embodiments are described with respect to endoscopic procedures, the present invention is suitable for any of a number of alternate applications requiring a guide sheath transmitting rotational forces therealong. For example, the exemplary embodiment of the present invention may also be used to allow for or improve rotation in smaller medical devices including but not limited to hemostatis clips.

Devices and methods according to the present invention employ a coiled guide sheath 100 with a lumen passing therethrough for receiving therein an endoscope and/or other medical device. The coiled guide sheath 100 according to the invention transmits rotation therealong so that a rotational force applied to a proximal end thereof causes a corresponding rotation of the distal end. For example, an exemplary coil sheath according to the invention is formed as a unibody structure relying on mechanical interaction between adjacent ones of the turns of the coil to transmit rotation therealong. It is noted that the use of the term distal herein refers to a direction extending away from a user of the device when the device is in an operative position while proximal refers to the toward the user. For example, the proximal portion of devices according to the invention remain external to the body when in an operative position while the distal end is inserted through a natural body lumen to a target site.

Known coils embody a multitude of parameter combinations selected in an attempt to conform the performance of the coil to a procedure to be performed. Some of these parameters include whether the pitch of the coil is open or closed, whether the wire is round or flat, the dimensions of the wire and the coil, and an amount of preload on a closed pitch coil, as those skilled in the art will understand. Although manipulation of these parameters has enabled the achievement of many design criteria including, for example, desired coil rigidity or flexibility, it is desired to provide a coil having an improved ability to transmit rotation therealong.

For example, one prior art coil includes adjacent turns of the coil welded together at a plurality of discrete location. Though this embodiment secures the turns together so as to increase rotational performance, the securing of these adjacent turns reduces the flexibility of the coil sheath. Furthermore, the welding process is expensive significantly increasing the cost of the device.

Figure 1:
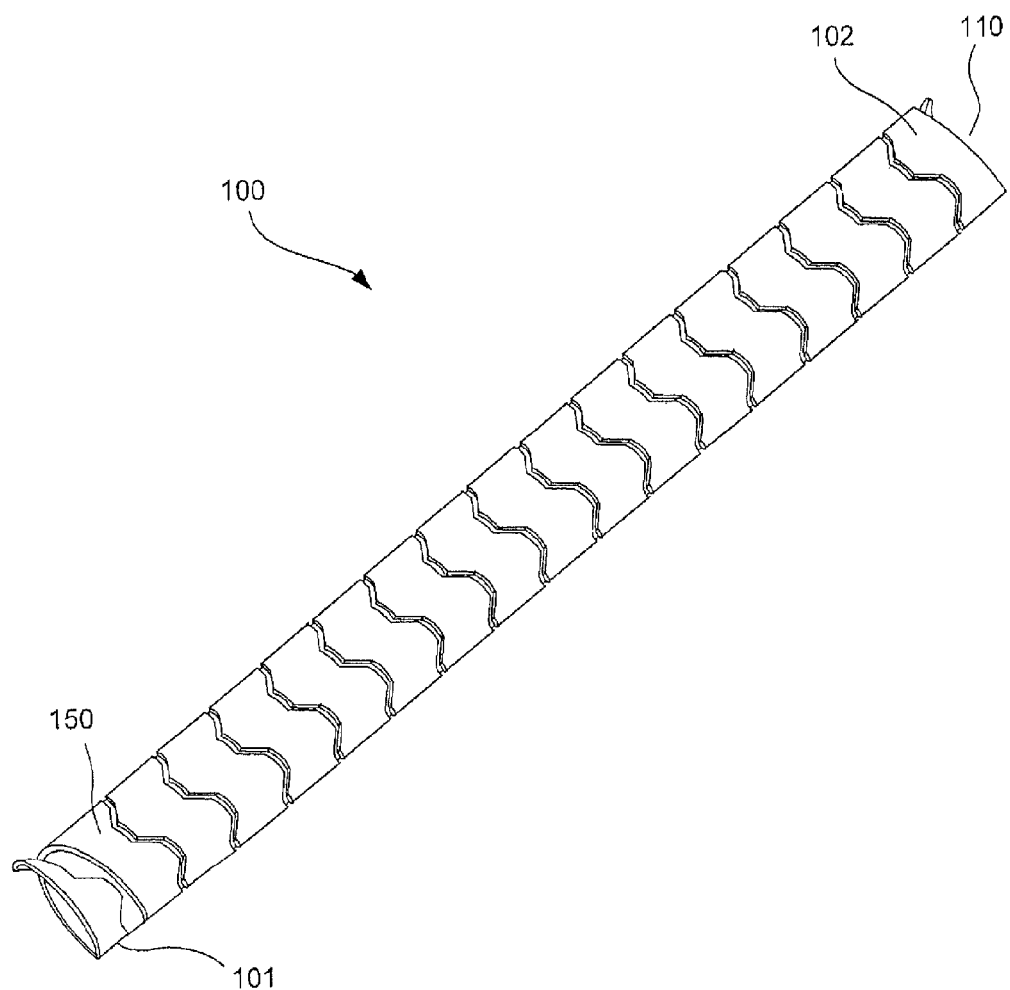
FIG. 1 is a perspective view of a flexible conduit according to a first embodiment of the present invention.

An exemplary embodiment of the present invention is shown with respect to FIG. 1, which shows a coiled sheath 100 forming a working channel 110 extending therethrough from a proximal end 101 to a distal end 102. The coiled sheath 101 is formed, for example, as a substantially helical coil comprised of a unibody wire substantially flat on radially inner and outer surfaces with a thickness of the wire transverse to a path of the coil (i.e., transverse to the path along which the wire is wound) varying to form a wave pattern. The wave pattern may be an inherent property of the design of the wire or ribbon before the wire is wound into a helix. Alternatively, the wave pattern may be imparted to the coil as a part of the winding or a subsequent process. Although the embodiments disclosed herein describe coils formed of wire, those skilled in the art will understand that this term is applied herein to refer to traditional wires with circular cross-sections as well as to flat ribbons and other shapes of metal which may be would to form flexible conduits as described herein. Furthermore, the coiled sheath 100 may be formed of any material other than metal, including, but not limited to polymers and ceramics. In a preferred embodiment, the coiled sheath may be formed of a plastic when formed with a diameter exceeding 1 cm. In such an embodiment, a thermoplastic material may be extruded and interlocking features formed thereon via a continuous method such as knurling. The thermoplastic may then be formed into a coil around a mandrel (not shown).

The wave pattern is selected relative to the diameter and pitch of the helix so that the troughs of the wave pattern of each turn of the coil mate with the peaks of the wave patterns of adjacent turns of the coil. Thus, adjacent turns of the coil are locked to one another and relative rotation therebetween is resisted. This allows the coiled sheath 100 to efficiently transmit to the distal end 102 thereof rotational forces applied to the proximal end 101. More specifically, when a torsional force is applied to the coiled sheath 100 at the proximal end 101, each of the turns of the coiled sheath 101 mechanically interact with adjacent turns of the coil to transmit the torsional force along the length of the coiled sheath 100. In a preferred embodiment, the angular distance between each of the individual coils of the coiled sheath 100 is minimized (e.g., during the winding process) to increase the mechanical interaction between adjacent coils. In one embodiment, the coiled sheath 100 is constructed as a closed pitch coil with a preload representative of a compressive force holding the individual coils in close contact with one another. The preload applied in this embodiment is preferably selected to reduce an angular distance between the individual coils to the maximum extent which still retains the degree of flexibility required of the coiled sheath 100 to enable the traversing of tortuous paths in the lumen into which it is to be inserted and to allow for controlled rotation of the coiled sheath 100.

It is noted that, in some instances, it may not be desirable to employ a closed pitch coil with a preload. Rotational movement may still be achieved in these instances after inducing an initial amount of deformation. This deformation may be achieved as a result of torsional input requiring the individuals coils of the coiled sheath 100 to deform until mechanical interaction between each of the adjacent coils is achieved. Alternatively, the coiled sheath 100 may be deformed along a curved path, wherein the deformation may cause the individual coils to mechanically interact with another.

The wave pattern of the wire or ribbon of the embodiment of FIG. 1 may be varied in a number of different ways to achieve the desired balance between rotational (torsional) stiffness and longitudinal flexibility. For example, the wavelength of the wave pattern may be reduced so that a greater number of waves may be accommodated in each turn of the coil. The increased number of waves per unit length of wire increases the overall rigidity of the coiled sheath 100 by increasing frictional forces between the individual turns of the coiled sheath 100. The frictional force between each of the individual turns of the coil may also be increased by knurling the contacting surfaces of the turns or otherwise roughening the contacting surfaces of the turns. Those skilled in the art will understand that sanded and rough contacting surfaces increases the mechanical interaction between the turns of the coiled sheath 100.

Figure 2:
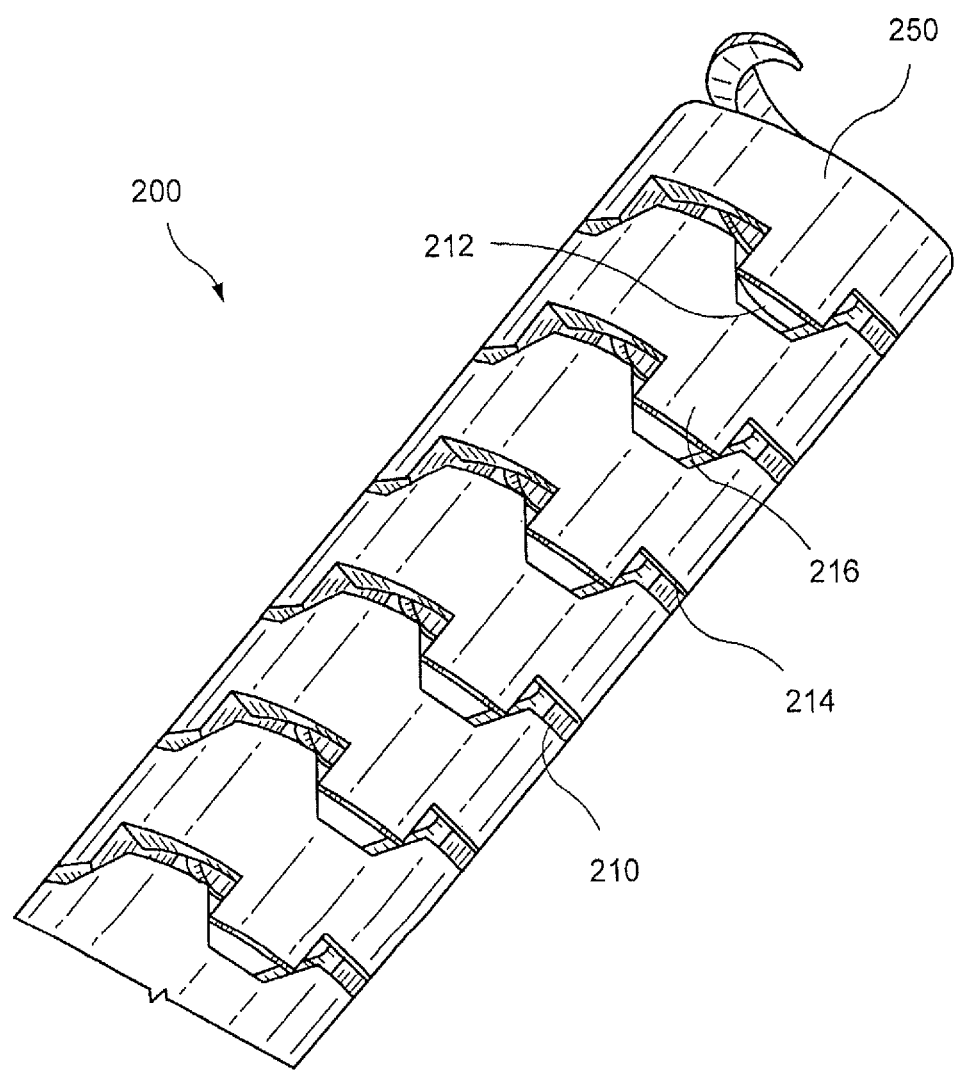
FIG. 2 is a perspective view of a flexible conduit according to a second embodiment of the present invention.

As would be understood by those skilled in the art, any of a wide variety of patterns of variations in the shape of the wire along its length may be employed to obtain the desired mechanical interaction between adjacent turns thereof while retaining a desired level of longitudinal flexibility. For example as shown in FIG. 2, the coiled sheath 200 of the present invention may form a first pattern on one side of the wire and a second pattern on the opposite side. A proximal side of the wire forming the coiled sheath 200 of FIG. 2 extends along a wave pattern including a plurality of substantially trapezoidal projections 210 separated from one another by a corresponding plurality of substantially trapezoidal troughs 212. The distal side of the wire includes a plurality of substantially straight portions 214 substantially parallel to the helical path of the coiled sheath 200 separated from one another by a plurality of substantially rectangular projections 216. The rectangular projections 216 are preferably separated from one another along the length of the wire by a distance substantially equal to a distance between the substantially trapezoidal troughs 212 so that each of the projections 216 is received within a corresponding trough 212 on an adjacent turn of the coiled sheath 200 while each of the trapezoidal projections 210 is received in a corresponding space between consecutive projections 216 (i.e., along a corresponding straight portion 214) of an adjacent turn of the coiled sheath 200. Those skilled in the art will recognize that the patterns on opposite sides of the wire may comprise any combination of complementary mating patterns on the abutting faces of adjacent turns of the coiled sheath 200 to establish the mechanical interference required to provide the desired transmission of torque along the length of the sheath 200. Furthermore, the heights and width of the troughs 212 and projections 216 may be selected to improve the performance of the coiled sheath 200.

It is noted that, although the exemplary embodiments are shown with substantially sharp edges, in practice the coiled sheaths 100 and 200 may comprise curved surfaces based on gear design principles for the interaction between coils. Employing such curves in this embodiment allows the effective transmission of torsional and rotational forces therealong the length of the coiled sheaths 100 and 200 while also allowing for self-alignment of the features during the winding process or while the coil is under load subsequent to the winding process. For example, the design may be selected to allow edges of adjacent turns of the ribbon or wire to interlock so that these adjacent turns of the coiled sheath 100 and 200 are pulled together as a toque is applied at one end.

Figure 3:
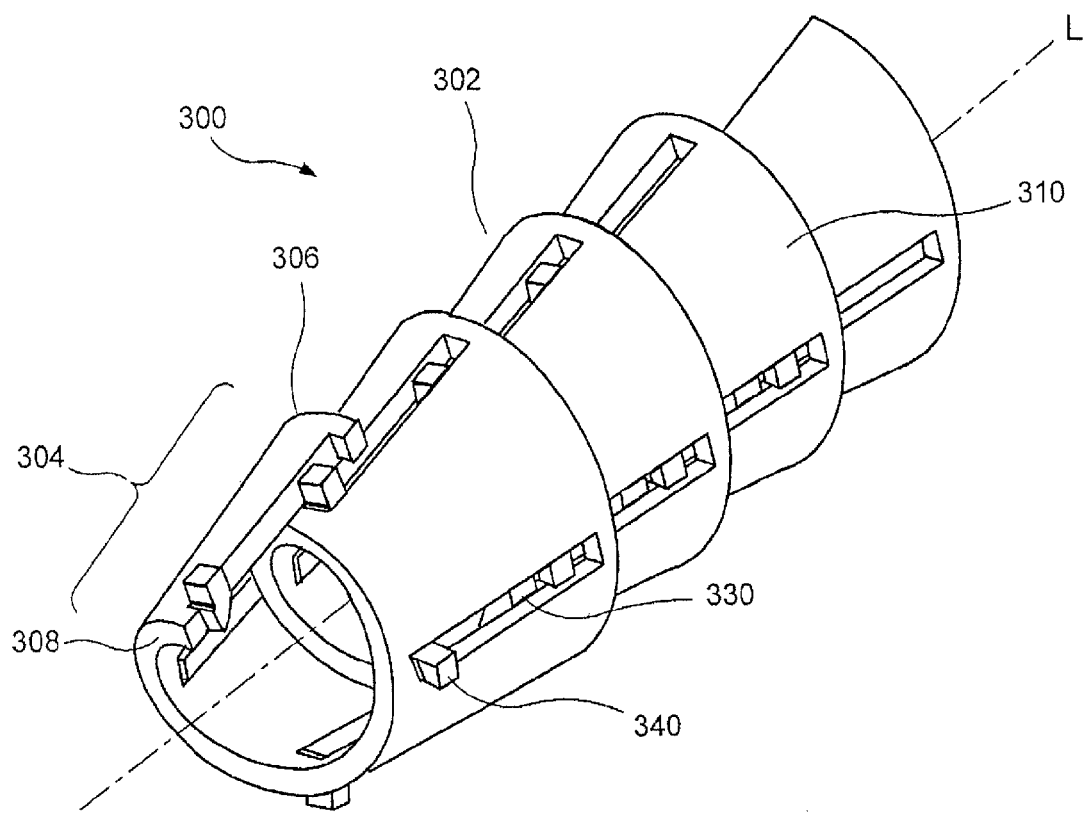
FIG. 3 is a perspective view of a flexible conduit according to a third embodiment of the present invention.

As shown in FIG. 3, a coiled sheath 300 according to an alternate embodiment of the present invention is formed from a bound wire 302 (or ribbon) with substantially smooth surfaces (i.e., without interlocking protrusions and indentations along the axis). Rather, progressive stamping or any other similar known technique may be used to form in the wire 302 a plurality of slots 330 oriented so that, when the wire 302 is bent into a helical coil, the slots 330 extend substantially parallel to a longitudinal axis L of the coiled sheath 300. In addition, a plurality of tabs 340 project radially away from the longitudinal axis L are formed in alignment with the slots 330 by, for example, bending radially outward portions of the wire 302 stamped out of the slots 330. The wire 302 is then bound into a helical coil with portions of adjacent turns 304 of the coil overlapping one another so that each tab 340 engages the slot 330 of an adjacent turn 304. As can be seen in FIG. 3, the wire 302 is preferably bent into a helical shape with a slight angular cast along the thickness of the wire 302 so that each turn of the coil is generally conical. This permits the narrowed distal end 308 of a first turn 304 to fit within the enlarged proximal end 306 of the adjacent turn 304 so that the tab 340 of the first turn 304 can be received within the slot 340 of the adjacent turn 304. Those skilled in the art will understand that the direction of the cast may be reversed so that the distal ends of the turns 304 are enlarged while the proximal ends 306 are narrowed. In addition, those skilled in the art will understand that the extent of the projection of the tabs 340 beyond the radially outer surface 310 of each turn 304 is preferably selected so that, when the coiled sheath 300 is bent to the maximum extent permitted, the end of each of the tabs 340 remains within the corresponding slot 330. The angle of the cast of the wire 302 is preferably selected relative to the size of the tabs 340 so that the tabs 340 do not project beyond an outer profile of the enlarged ends 306 of the turns of the coiled sheath 300.

The tabs 340 prevent adjacent turns 304 from rotating relative to one another, transmitting torque applied to one end of the coiled sheath 300 to the other end thereof. At the same time, the length of each of the slots 330 along the longitudinal axis L is preferably selected to be greater than a length of the corresponding tab 340 along the longitudinal axis L by an amount required to impart a desired degree of longitudinal flexibility to the coiled sheath 300. As would be understood by those skilled in the art, the width of each of the tabs 340 (i.e., thickness in a direction substantially perpendicular to the longitudinal axis) is selected relative to the width of the corresponding slot 330 to permit the tabs 340 to slide freely, or with a desired frictional resistance, therewithin. Thus, the length of the slot 330 along which each of the tabs 340 may slide dictates the permitted degree of bending of the coiled sheath 300 (i.e., the minimum radius around which the sheath 300 may be bent) along the longitudinal axis while the frictional engagement of the tabs 340 within the slots 330 dictates the force required to achieve the desired bending. Those skilled in the art will understand that this permitted degree of bending and/or the force required for bending may be constant along the length of the coiled sheath 300 or may be varied therealong by varying the dimensions of the tabs 340 and the corresponding slots 330 to alter the distance along which the various tabs 340 may slide as well as the resistance to this sliding.

The embodiment of FIG. 3 may also be modified in a number of ways without deviating from the scope of the invention. For example, one or both longitudinal surfaces of the wire 302 may be knurled to roughen the surface and increase the frictional force between each of the turns of the coiled sheath 300. In another embodiment, the flat surface of the wire 302 may be rolled and/or stamped to form ribs or small dents and/or protrusions. Since the wire 302 is wound in an overlapping manner, this increases the frictional force and mechanical interaction between the turns 304. To this end, tabs 340 may be constructed as folds (not shown) in the surface of the wire 302. An external edge of each of the folds (not shown) protruding into a slot 330 may act as a tab in this embodiment.

Figure 4:
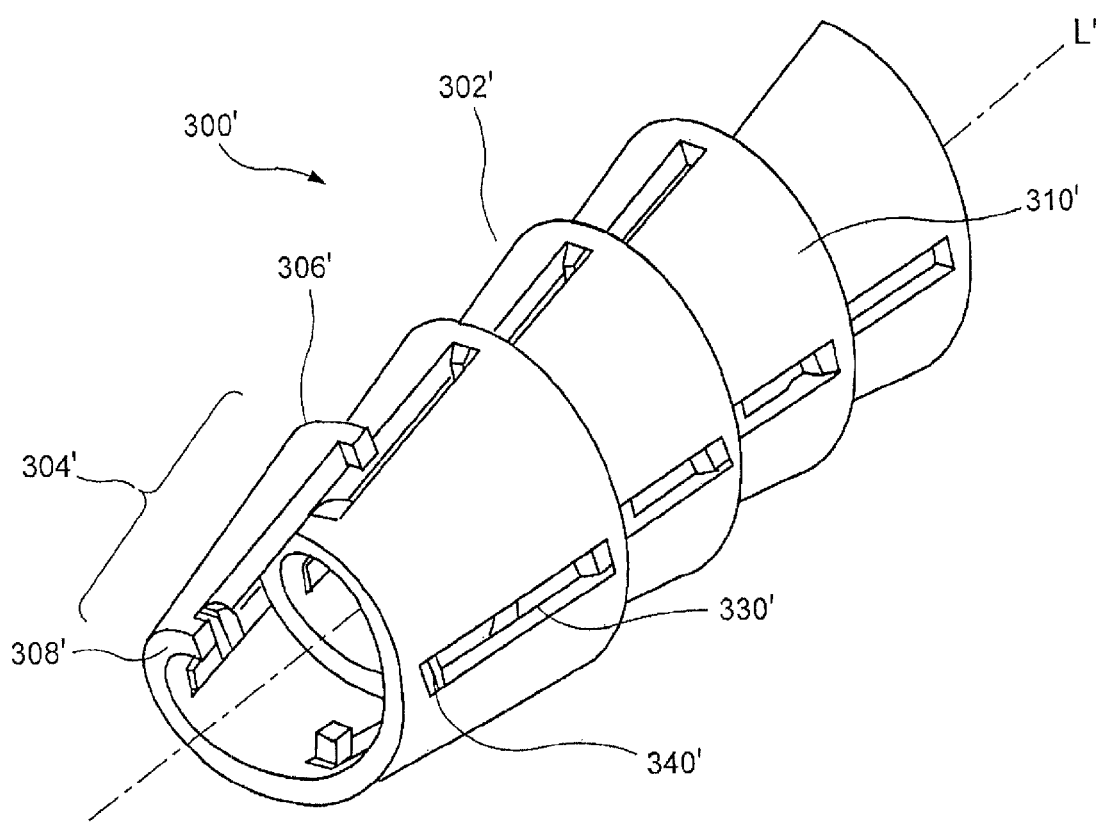
FIG. 4 is a perspective view of a flexible conduit according to a fourth embodiment of the present invention.

As shown in FIG. 4, a coiled sheath 300' according to yet another embodiment of the invention is substantially similar to the coil 300 of FIG. 3 except that the coil 300' includes tabs 340' bent radially inward toward the longitudinal axis L'. In this embodiment, each of the tabs 340' is formed near the enlarged end 306 of the turn 304 of the coil over a slot 330' of the reduced diameter portion 308' of an adjacent turn 304 received therewithin. With this arrangement, the outer surface 310' of the coiled sheath 300' remains substantially smooth minimizing the possibility of trauma and minimizing the required thickness of an outer sheath over the coiled sheath 300 and possibly eliminating the need for such an outer sheath altogether.

Furthermore, it is noted that although the present embodiment is described using rectangular tabs 340, 340', any of a number of differently shaped indentations and projections may be employed without deviating from the scope of the present invention. For example, dimples, burrs, or other features may be used in place of discrete tabs. It is noted that the inherent concept of the present embodiment is the engagement of a protrusion with a slot formed on an adjacent turn of a wire to prevent relative rotation between adjacent turns of a coil.

It is further noted that the present invention may be modified in a host of manners that may increase the friction force and mechanical interaction between each of the individual coils of the coiled sheath without deviating from the spirit and scope of the present invention.

The embodiments of FIGS. 1-4 have been described with respect to a single ribbon or wire wound into a helix. Those skilled in the art will understand that the single wire of the above-described embodiments may be replaced by 2 or more wires wound together in a coil so long as the turns of the various wires mechanically interact with adjacent turns of wire in the manner described above to prevent relative rotation therebetween. For example, the distal side of a first longitudinal length of wire may interact mechanically with the proximal side of a longitudinal length of a second wire and vice versa along their lengths with each of the wires forming alternating ones of the turns of the coiled sheath. In another example, a first wire containing a plurality of tabs similar to those described above in regard to FIG. 3 may be wound within or around a second wire including a corresponding set of slots as described above. In yet another example, a single plastic ribbon or strip may be coiled into a helical shape. Such an embodiment may offer particular advantages when employed with direct drive endoscopic systems.

Figure 5:
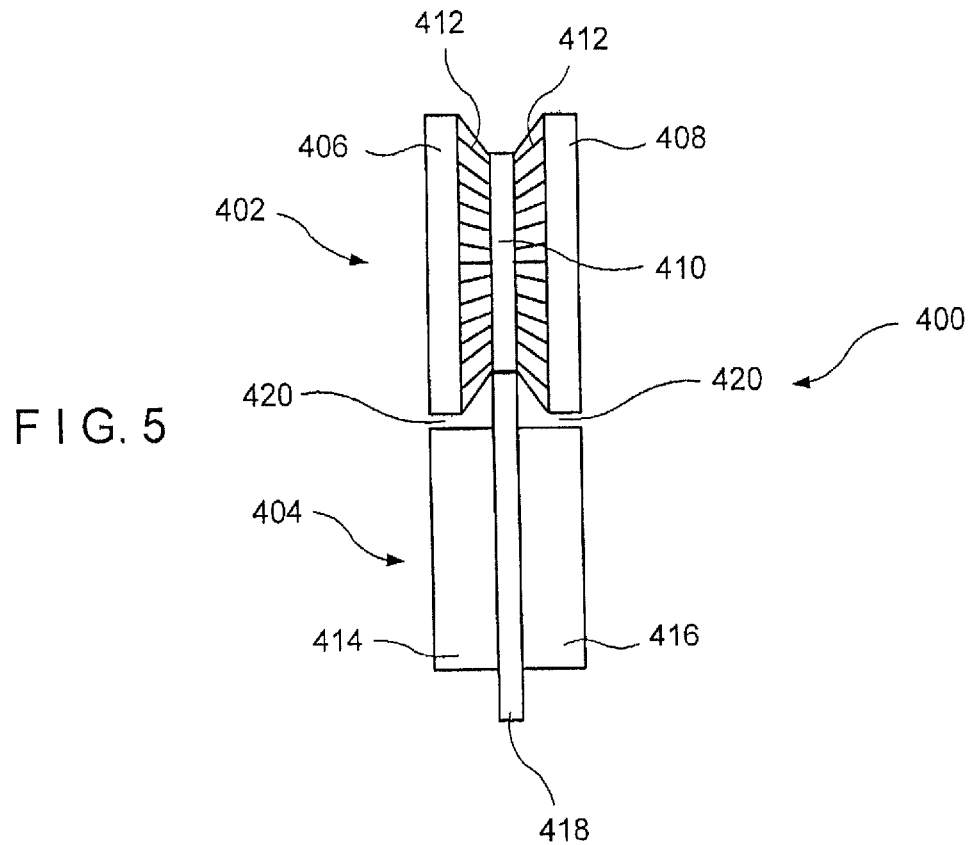
FIG. 5 is a first perspective view of a forming die according to the present invention.
Figure 6:
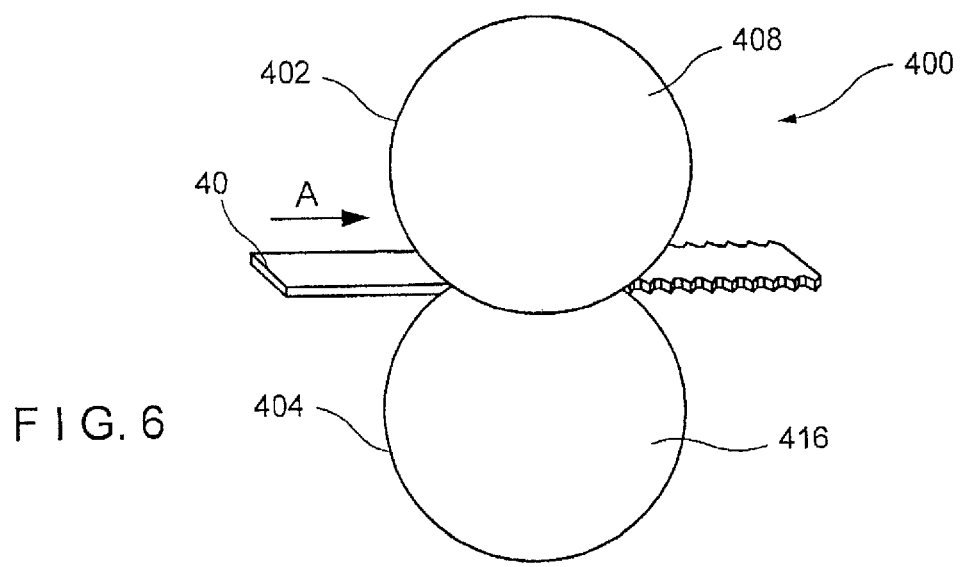
FIG. 6 is a second perspective view of the forming die of FIG. 5.

FIGS. 5-6 depict a forming die 400 according to an exemplary embodiment of the present invention. The forming die 400 may be used to shape the wire of the coiled sheath 100 or that of another ribbon or wire structure. Specifically, as described with respect to earlier embodiments, the wire or ribbon must be formed with features that interlock with one another when the wire or ribbon is coiled. The forming die comprises first and second forming wheels 402, 404 configured to engage one another. The first forming wheel 402 comprises a pair of lateral wheels 406, 408 encasing a medial wheel 410, the lateral wheels 406, 408 having a greater diameter than the medial wheel 410. The medial wheel 410 has a smooth outer circumference and is connected to the lateral wheels 406, 408 by angled surfaces 412. Specifically, the angled surfaces 412 link the smaller diameter medial wheel 410 with the increased diameter lateral wheels 406, 408. The second forming wheel 404 also comprises a pair of lateral wheels 414, 416 connected by a medial wheel 418. The medial wheel 418 has a greater diameter than the lateral wheels 414, 416, a diameter thereof being selected to permit a predetermined clearance 420 between the first and second forming wheels 402, 404 when the medial wheel 418 contacts the medial wheel 410. Specifically, the clearance 420 is configured to permit a wire such as the wire 40 to be inserted therethrough with a substantial friction fit sufficient to cause a knurling or keying thereof as the wire 40 is moved in the direction A as would be understood by those skilled in the art.

The first and second forming wheels 402, 404 may be held together within a housing (not shown). The housing (not shown) may be configured to change a relationship of the first and second wheels 402, 404 relative to one another as needed (i.e., to change a size of the clearance 420 depending on a thickness of the wire 40 or a desired pressure to be applied thereto). In another embodiment of the present invention, the first and second forming wheels 402, 404 may be replaced by a single component permitting the insertion of a wire into a clearance area in substantially the same manner described above. In yet another embodiment, laterally separated sides of the wire may be formed by separate forming dies, which may be linked to one another via a gear system. Thus, as the wire is moved through the gear system, each side wall travels through a separate forming die to be shaped. In yet another embodiment, edges of the wire may be laser cut or the wire may undergo progressive stamping to affect a shape thereof, as those skilled in the art will understand. It is further noted that any combination and modification of the aforementioned embodiment may be employed to permit the keying of materials of different sizes and densities.

Those skilled in the art will understand that the described exemplary embodiments of the present invention may be altered without departing from the spirit or scope of the invention. Thus, it is to be understood that these embodiments have been described in an exemplary manner and are not intended to limit the scope of the invention which is intended to cover all modifications and variations of this invention that come within the scope of the appended claims and their equivalents.

What is claimed is:

1. A coil transmitting a torque, comprising:
a wire extending along a helical path about a longitudinal axis such that portions of adjacent turns of the wire overlap one another, the wire including a plurality of slots extending laterally therethrough such that a length of each of the slots extends longitudinally along the coil and a plurality of tabs extending radially therefrom such that each of the tabs is received in a corresponding one of the slots extending through an overlapping portion of an adjacent turn of the wire, wherein the wire is bent along the helical path at an angular cast along a thickness of the wire so that each turn of the coil is conical.

2. The coil of claim 1, wherein the tabs project radially outward away from the longitudinal axis.

3. The coil of claim 1, wherein the tabs project radially inward toward the longitudinal axis so that an outer surface of the wire is smooth.

4. The coil of claim 1, wherein an extent of a projection of the tabs beyond a surface of the wire is selected so that when the coil is bent to a maximum extent relative to the longitudinal axis, the end of each of the tabs remain within the corresponding one of the slots.

5. The coil of claim 1, wherein each of the tabs are formed by bending a portion of the wire stamped out to form the slots.

6. The coil of claim 1, wherein the length of each of the slots is longer than the corresponding one of the tabs received therein so that the tabs are slidably along the length of the slots to permit a bending of the wire along the longitudinal axis.

7. The coil of claim 1, wherein a size of the tabs relative to the slots prevents adjacent turns of the wire from rotating relative to one another.

8. A coil transmitting a torque, comprising:
a wire extending along a helical path about a longitudinal axis such that portions of adjacent turns of the wire overlap one another, the wire including a plurality of slots extending laterally therethrough such that a length of each of the slots extends longitudinally along the coil and a plurality of tabs extending radially therefrom such that each of the tabs is received in a corresponding one of the slots extending through an overlapping portion of an adjacent turn of the wire, wherein the wire is bent along the helical path at an angular cast along a thickness of the wire so that each turn of the coil is conical, wherein distal ends of each turn are narrowed while proximal ends of each turn are enlarged so that the narrowed distal end of one turn fits within the enlarged proximal end of an adjacent turn.

9. A coil transmitting a torque, comprising:
a wire extending along a helical path about a longitudinal axis such that portions of adjacent turns of the wire overlap one another, the wire including a plurality of slots extending laterally therethrough such that a length of each of the slots extends longitudinally along the coil and a plurality of tabs extending radially therefrom such that each of the tabs is received in a corresponding one of the slots extending through an overlapping portion of an adjacent turn of the wire, wherein the wire is bent along the helical path at an angular cast along a thickness of the wire so that each turn of the coil is conical, wherein distal ends of each turn are enlarged while proximal ends of each turn are narrowed so that the narrowed proximal end of one turn fits within the enlarged distal end of an adjacent turn.

10. A coil transmitting a torque, comprising:
a wire extending along a helical path about a longitudinal axis such that portions of adjacent turns of the wire overlap one another, the wire including a plurality of slots extending laterally therethrough such that a length of each of the slots extends longitudinally along the coil and a plurality of tabs extending radially therefrom such that each of the tabs is received in a corresponding one of the slots extending through an overlapping portion of an adjacent turn of the wire, wherein the wire is bent along the helical path at an angular cast along a thickness of the wire so that each turn of the coil is conical, wherein an angle of the cast is selected relative to a size of the tabs so that the tabs do not extend beyond a radially outermost profile of the wire.

11. A coil transmitting a torque, comprising:
a wire extending along a longitudinal axis, the wire including a plurality of slots extending laterally therethrough from a first longitudinal surface thereof to a second longitudinal surface thereof and a plurality of tabs extending radially from one of the first and second longitudinal surfaces in alignment with the plurality of slots so that, when the wire is wound into a helical coil such that adjacent turns of the coil overlap one another, each of the tabs is received within a corresponding one of the slots along an overlapping portion of an adjacent turn of the wire, the slots extending longitudinally along the helical coil.

12. The coil of claim 11, wherein, a length of the slots is selected so that, when the wire is wound into the helical coil, the tabs are permitted to slide along a length of the slots.

13. The coil of claim 11, wherein a width of the slots is selected so that, when the wire is wound into the helical coil, the slots prevents adjacent turns of the wire from rotating relative to one another.

14. The coil of claim 11, wherein the tabs are formed by bending a portion of the wire stamped out to define the slots.

15. The coil of claim 11, wherein one of the first and second longitudinal surfaces are roughened so that, when the wire is wound into the helical coil with adjacent turns of the wire overlapping one another, a frictional force between the adjacent turns is increased.

16. The coil of claim 11, wherein a projection of the tabs from one of the first and second surfaces is selected so that, when the wire is wound in the helical coil, the tabs remain engaged with the corresponding one of the slots when the helical coil is bent relative to a longitudinal axis thereof.

* * * * *